United States Patent
Doll et al.

(10) Patent No.: US 11,338,079 B2
(45) Date of Patent: May 24, 2022

(54) MEDICAL INSTRUMENT

(71) Applicant: Karl Storz SE & Co. KG, Tuttlingen (DE)

(72) Inventors: Frank Doll, Talheim (DE); Stefan Rehbein, Immendigen-Hattingen (DE); Uwe Wittke, Tuttlingen-Möhringen (DE); Rainer Hermle, Gosheim (DE); Oliver Löffler, Boll (DE); Udo Nagele, Wörgl (AT)

(73) Assignee: KARL STORZ SE & CO. KG, Tuttlingen (DE)

( * ) Notice: Subject to any disclaimer, the term of this patent is extended or adjusted under 35 U.S.C. 154(b) by 153 days.

(21) Appl. No.: 16/026,124

(22) Filed: Jul. 3, 2018

(65) Prior Publication Data
US 2019/0009016 A1 Jan. 10, 2019

(30) Foreign Application Priority Data
Jul. 10, 2017 (DE) ...................... 10 2017 115 379.9

(51) Int. Cl.
*A61M 3/02* (2006.01)
*A61B 1/015* (2006.01)
(Continued)

(52) U.S. Cl.
CPC ........... *A61M 3/0233* (2013.01); *A61B 1/015* (2013.01); *A61B 1/12* (2013.01); *A61B 18/1485* (2013.01);
(Continued)

(58) Field of Classification Search
CPC ............ A61M 3/0283; A61M 5/16881; A61M 2205/3334; A61M 2039/2473–248;
(Continued)

(56) References Cited

U.S. PATENT DOCUMENTS 1,128,445 A * 2/1915 Henning ............. F16K 37/0016
137/556.6
3,850,162 A * 11/1974 Iglesias .............. A61B 1/00091
600/105
(Continued)

FOREIGN PATENT DOCUMENTS

DE 199 17 624 A1 12/2000
DE 102007003690 A1 8/2008
(Continued)

OTHER PUBLICATIONS

Search Report, DE 10 2017 115 379.9, dated Jan. 24, 2018 (8 pp.).
Search Report, EP 18 17 7494, dated Oct. 24, 2018 (10 pp.).

*Primary Examiner* — Bhisma Mehta
*Assistant Examiner* — John J Crawford
(74) *Attorney, Agent, or Firm* — Eversheds Sutherland (US) LLP

(57) ABSTRACT

A medical instrument for diagnostic, therapeutic, or surgical measures in a cavity in the body of a patient may include a proximal region, which is provided and designed for arrangement outside the body, a distal region, which is provided and designed for arrangement inside a cavity in the body, a supply structure for delivering a fluid to the cavity, wherein the supply structure reaches from a first coupling in the proximal region of the medical instrument to an outlet in the distal region, and a discharge structure for discharging a fluid from the cavity, wherein the discharge structure reaches from an inlet in the distal region of the medical instrument to a second coupling in the proximal region of the medical instrument. The flow resistance of the supply structure is greater than the flow resistance of the discharge structure.

17 Claims, 5 Drawing Sheets

(51) Int. Cl.
    *A61M 1/00*     (2006.01)
    *A61B 1/12*     (2006.01)
    *A61M 39/24*     (2006.01)
    *A61M 39/22*     (2006.01)
    *A61B 18/00*     (2006.01)
    *A61B 18/14*     (2006.01)
    *A61B 1/307*     (2006.01)

(52) U.S. Cl.
    CPC .......... *A61M 1/0058* (2013.01); *A61M 39/24* (2013.01); *A61B 1/307* (2013.01); *A61B 2018/00744* (2013.01); *A61B 2217/005* (2013.01); *A61B 2217/007* (2013.01); *A61B 2218/002* (2013.01); *A61M 39/22* (2013.01); *A61M 2039/242* (2013.01); *A61M 2039/2473* (2013.01); *A61M 2205/3334* (2013.01)

(58) Field of Classification Search
    CPC .......... A61M 3/0233; A61M 2039/224; A61M 1/0041; A61B 1/015; A61B 1/126; A61B 1/12; A61B 1/0058; A61B 2218/001; A61B 2018/00744; Y10T 137/86549; F16K 11/0704; F16K 31/563

USPC ........................................................ 251/207
    See application file for complete search history.

(56) References Cited

U.S. PATENT DOCUMENTS

| | | | | |
|---|---|---|---|---|
| 3,900,022 | A | * | 8/1975 | Widran .................... A61B 1/12 600/105 |
| 5,005,604 | A | | 4/1991 | Aslanian |
| 7,921,874 | B2 | * | 4/2011 | Tekulve ................ F16K 15/148 137/513.3 |
| 2004/0220452 | A1 | * | 11/2004 | Shalman ................ A61B 1/126 600/157 |
| 2012/0010464 | A1 | | 1/2012 | Adams et al. |
| 2012/0271110 | A1 | | 10/2012 | Kumar et al. |
| 2016/0303310 | A1 | * | 10/2016 | Dai ..................... A61M 3/0283 |
| 2017/0100016 | A1 | * | 4/2017 | Begg ................. A61B 1/00071 |

FOREIGN PATENT DOCUMENTS

| | | |
|---|---|---|
| DE | 10 2008 050 991 A1 | 4/2010 |
| DE | 10 2015 014 254 A1 | 5/2017 |
| WO | WO-2016165806 A1 * 10/2016 ......... A61B 1/00068 |

* cited by examiner

MEDICAL INSTRUMENT

TECHNICAL FIELD

The present invention relates to a resectoscope or a cystoscope or a hysteroscope or another medical instrument for diagnostic, therapeutic and/or surgical measures in a cavity in the body of a patient, with a supply structure for delivering a fluid to the cavity and a discharge structure for discharging a fluid from the cavity.

BACKGROUND OF THE INVENTION

A resectoscope, a cystoscope, a hysteroscope or another medical instrument for diagnostic, therapeutic and/or surgical measures in a hollow organ or in another natural or artificial cavity in the body of a patient generally has fluid channels for delivering a rinsing fluid and for discharging the rinsing fluid from the cavity. In a proximal region of such a medical instrument, two valves are provided, by means of which, on the one hand, the inflow of the fresh rinsing fluid and, on the other hand, the outflow of fluid from the cavity can be controlled. In order to fill and/or widen the cavity, the valve in the inflow is opened and the valve in the outflow is closed. Thereafter, the medical personnel manually adjust the valves such that a dynamic equilibrium is set. The resulting degree of filling and pressure in the cavity are dependent on the adjustment of the two valves and therefore on the experience and attentiveness of the medical personnel. Errors on the part of the medical personnel can in particular lead to too high a pressure in the cavity and may consequently cause damage to the patient.

SUMMARY OF THE INVENTION

An object of the present invention is to create an improved medical instrument which in particular affords greater safety against incorrect operation.

This object is achieved by the subjects of the independent claims.

Developments are set out in the dependent claims.

A medical instrument for diagnostic, therapeutic or surgical measures in a cavity in the body of a patient comprises a proximal region, which is provided and designed for arrangement outside the body, a distal region, which is provided and designed for arrangement inside a cavity in the body, a supply structure for delivering a fluid to the cavity, wherein the supply structure reaches from a first coupling in the proximal region of the medical instrument to an outlet in the distal region, and a discharge structure for discharging a fluid from the cavity, wherein the discharge structure reaches from an inlet in the distal region of the medical instrument to a second coupling in the proximal region of the medical instrument, wherein the flow resistance of the supply structure is greater than the flow resistance of the discharge structure.

The medical instrument is provided and designed in particular for diagnostic, therapeutic and/or surgical measures in a hollow organ or in another natural or artificially created cavity in the body of a patient.

The medical instrument is in particular a resectoscope or a cystoscope or a hysteroscope. The proximal region of the medical instrument can comprise a work element, which facilitates a precise manual movement of a laser probe or of a monopolar or bipolar electrosurgical probe, and/or other structures for manual handling and control of the medical instrument. The distal region of the medical instrument is formed in particular by a shaft, inside which a large part of the supply structure and a large part of the discharge structure can be provided. If the distal region of the medical instrument is formed by a shaft, the outlet of the supply structure and/or the inlet of the discharge structure can be provided at or near the distal end of said shaft.

The first coupling and the second coupling each comprise in particular a Luer coupling or a Luer lock coupling and/or a hose coupling.

If the medical instrument has several different possible or at least intended configurations during its intended use, i.e. the operation of the medical instrument is possible or intended in several different configurations, the flow resistance of the supply structure is greater than the flow resistance of the discharge structure in each possible configuration or each intended configuration of the medical instrument.

The fact that the flow resistance of the supply structure is greater than the flow resistance of the discharge structure has the effect that a pressure in the cavity is established that is closer to the pressure present at the second coupling than to the pressure present at the first coupling. The pressure present in the cavity is therefore generally lower than the maximum pressure attainable with a conventional medical instrument with otherwise the same configuration. The risk of injury to a patient as a result of too high a pressure in the cavity is thereby greatly reduced.

In a medical instrument as described here, the discharge structure in particular, during the intended use of the medical instrument, is not closable or not unconditionally closable.

A medical instrument for diagnostic, therapeutic or surgical measures in a cavity in the body of a patient comprises a proximal region, which is provided and designed for arrangement outside the body, a distal region, which is provided and designed for arrangement inside a cavity in the body, a supply structure for delivering a fluid to the cavity, wherein the supply structure reaches from a first coupling in the proximal region of the medical instrument to an outlet in the distal region, and a discharge structure for discharging a fluid from the cavity, wherein the discharge structure reaches from an inlet in the distal region of the medical instrument to a second coupling in the proximal region of the medical instrument, wherein the discharge structure is not closable or not unconditionally closable during the intended use of the medical instrument.

The intended use comprises in particular all configurations and scenarios for which the medical instrument is authorized. Since the discharge structure is not closable in the intended use, the pressure in the cavity cannot rise as far as the pressure present at the first coupling, and instead it always remains below the pressure present at the first coupling.

The discharge structure is not unconditionally closable if it is not closable or only closable such that it is closed or remains closed only under certain conditions. The discharge structure is in particular not unconditionally closable if it is closable only in such a way that the discharge structure opens as a result of a predetermined pressure being exceeded.

In a medical instrument as described here, the discharge structure in particular comprises a safety valve which opens if a predetermined pressure in the discharge structure is exceeded.

A medical instrument for diagnostic, therapeutic or surgical measures in a cavity in the body of a patient comprises a proximal region, which is provided and designed for arrangement outside the body, a distal region, which is provided and designed for arrangement inside a cavity in the body, a supply structure for delivering a fluid to the cavity, wherein the supply structure reaches from a first coupling in the proximal region of the medical instrument to an outlet in the distal region, and a discharge structure for discharging a fluid from the cavity, wherein the discharge structure reaches from an inlet in the distal region of the medical instrument to a second coupling in the proximal region of the medical instrument, wherein the discharge structure comprises a safety valve which opens if a predetermined pressure in the discharge structure is exceeded.

The safety valve can have a configuration that is adjustable manually or in some other way and is open independently of the pressure present in the discharge structure. Alternatively, the safety valve can be designed to open only dependently on the pressure present in the discharge structure. The safety valve can moreover be designed to close if the predetermined pressure is not reached or if a further, lower predetermined pressure is not reached. Alternatively, the safety valve can be designed such that, after it has been opened as a result of the predetermined pressure being exceeded, it can be closed again only by manual or other control.

In a medical instrument as described here, at least either the supply structure has a flow resistance means which substantially determines the flow resistance of the supply structure, or the discharge structure has a flow resistance means which substantially determines the flow resistance of the discharge structure.

The one or more flow resistance means are in particular arranged in or near the proximal region of the medical instrument. In particular, a flow resistance means is arranged between the first coupling and a first line which is arranged in a shaft of the medical instrument and which is a component part of the supply structure. Alternatively or additionally, a flow resistance means can be arranged between a second line, which is arranged in the shaft and is a component part of the discharge structure, and the second coupling.

If the supply structure has a flow resistance means, the fluid properties, pressures and flows during the intended use are such that the flow resistance of this flow resistance means is in particular at least one tenth or at least one fifth or at least one quarter or at least one third or at least half or at least two thirds or at least three quarters or at least four fifths or at least nine tenths of the flow resistance of the entire supply structure. If the discharge structure has a flow resistance means, the fluid properties, pressures and flows during the intended use are such that the flow resistance of this flow resistance means is in particular at least half or at least two thirds or at least three quarters or at least four fifths or at least nine tenths of the flow resistance of the entire discharge structure. If the medical instrument has several different configurations, this applies in particular for each possible configuration or for at least each intended configuration of the medical instrument.

In a medical instrument as described here, the smallest cross-sectional area of the supply structure or of the discharge structure is present in particular in the flow resistance means.

If the supply structure has a flow resistance means, the smallest cross-sectional area of the supply structure is present in particular in the flow resistance means. If the discharge structure has a flow resistance means, the smallest cross-sectional area of the discharge structure is present in particular in the flow resistance means.

In a medical instrument as described here, the flow resistance means has in particular an adjustable flow resistance.

The flow resistance of the flow resistance means can be modifiable, for example, by modifying the cross-sectional area of the flow resistance means or by modifying the configuration of the flow resistance means. Different values of the flow resistance of the flow resistance means result in different pressures in a cavity in which diagnostic, therapeutic or surgical measures are performed by means of the medical instrument.

In a medical instrument as described here, the flow resistance means has in particular a finite number of alternative predetermined configurations with different flow resistances, wherein the flow resistance means is provided and designed to be operated exclusively in the predetermined configurations.

A medical instrument for diagnostic, therapeutic or surgical measures in a cavity in the body of a patient comprises a proximal region, which is provided and designed for arrangement outside the body, a distal region, which is provided and designed for arrangement inside a cavity in the body, a supply structure for delivering a fluid to the cavity, wherein the supply structure reaches from a first coupling in the proximal region of the medical instrument to an outlet in the distal region, a discharge structure for discharging a fluid from the cavity, wherein the discharge structure reaches from an inlet in the distal region of the medical instrument to a second coupling in the proximal region of the medical instrument, and a flow resistance means in the supply structure or in the discharge structure, wherein the flow resistance means has a finite number of alternative predetermined configurations with different flow resistances, and wherein the flow resistance means is provided and designed to be operated exclusively in the predetermined configurations.

The flow resistance means has in particular fewer than ten, for example two, three, four or five alternative predetermined configurations with different flow resistances. The flow resistance means has in particular several different channels or bores with different cross sections and different flow resistances, wherein fluid flows through different channels or bores in different configurations of the flow resistance means.

In a medical instrument as described here, the flow resistance means has in particular a latching structure which permits only the predetermined configurations of the flow resistance means or which prefers the predetermined configurations over other configurations.

The latching structure comprises, for example, an elastically deflectable latching lug or a spring-loaded ball which can engage in one of several grooves or other recesses. In each of the predetermined configurations of the flow resistance means, the latching lug or the ball engages in one of the grooves or recesses.

Alternatively, the latching structure can comprise, for example, one or more magnets and optionally one or more soft-magnetic members. In this case, in the predetermined configurations, two opposite poles of different magnets lie opposite each other, or a pole of one magnet has a minimal spacing from a soft-magnetic structure.

In a medical instrument as described here, the flow resistance means has in particular a rotatable member, or a member movable along a straight or curved path, with several through-bores, wherein fluid can flow through one or more of the through-bores in each predetermined configuration of the flow resistance means.

The flow resistance means is in particular a plug valve with a conical plug which is rotatable about its axis of symmetry and has the through-bores substantially orthogonal to its axis of symmetry. Alternatively, the movable member can be designed, for example, as a slide movable along a straight path, with several through-bores arranged next to one another.

In a medical instrument as described here, the through-bores have in particular different cross sections, wherein fluid can flow through one of the through-bores in each predetermined configuration of the flow resistance means.

The through-bores are in particular arranged in the described movable member in such a way that, upon movement of the member during the closing of a through-bore, an adjacent through-bore is already opened. This arrangement can have the effect that the flow resistance means is never completely closed, even in all configurations between the predetermined configurations.

In a medical instrument as described here, the discharge structure in particular has a flow resistance means, wherein the flow resistance means of the discharge structure does not completely close the discharge structure in any possible configuration or any intended configuration of the medical instrument, or the flow resistance means of the discharge structure does not unconditionally completely close the discharge structure in any possible configuration or in any intended configuration of the medical instrument.

The flow resistance means of the discharge structure only conditionally closes the discharge structure, for example, if it closes the discharge structure only in the presence of a pressure in the discharge structure below a predetermined threshold value.

The intended configurations of the medical instrument are in particular the intended configurations of the flow resistance means of the discharge structure. The possible configurations of the medical instrument are in particular the possible configurations of the flow resistance means of the discharge structure. Since the flow resistance means of the discharge structure does not completely close the discharge structure in any intended configuration and optionally also in any possible configuration of the medical instrument, the pressure in a cavity in the body of a patient in which a diagnostic, therapeutic or surgical measure is performed by means of the medical instrument always remains less than the pressure present at the first coupling.

In a medical instrument as described here, provision is in particular made that the supply structure and the discharge structure each has a flow resistance means, wherein the flow resistance of the flow resistance means of the supply structure is greater than the flow resistance of the flow resistance means of the discharge structure.

In particular, the flow resistance of the flow resistance means of the supply structure is greater than the flow resistance of the flow resistance means of the discharge structure in each intended configuration or in each possible configuration of the medical instrument.

If the flow resistance of the flow resistance means of the supply structure is greater than the flow resistance of the flow resistance means of the discharge structure and the flow resistances of the other component parts of the supply structure and of the discharge structure are equal, a pressure established in the cavity is closer to the pressure present at the second coupling than to the pressure present at the first coupling. This pressure, lower by comparison with conventional medical instruments, protects the patient.

In a medical instrument as described here, provision is made in particular that the minimal cross section of the flow resistance means of the supply structure is smaller than the minimal cross section of the flow resistance means of the discharge structure.

BRIEF DESCRIPTION OF THE DRAWINGS

BRIEF DESCRIPTION OF THE FIGURES

Figure 1:
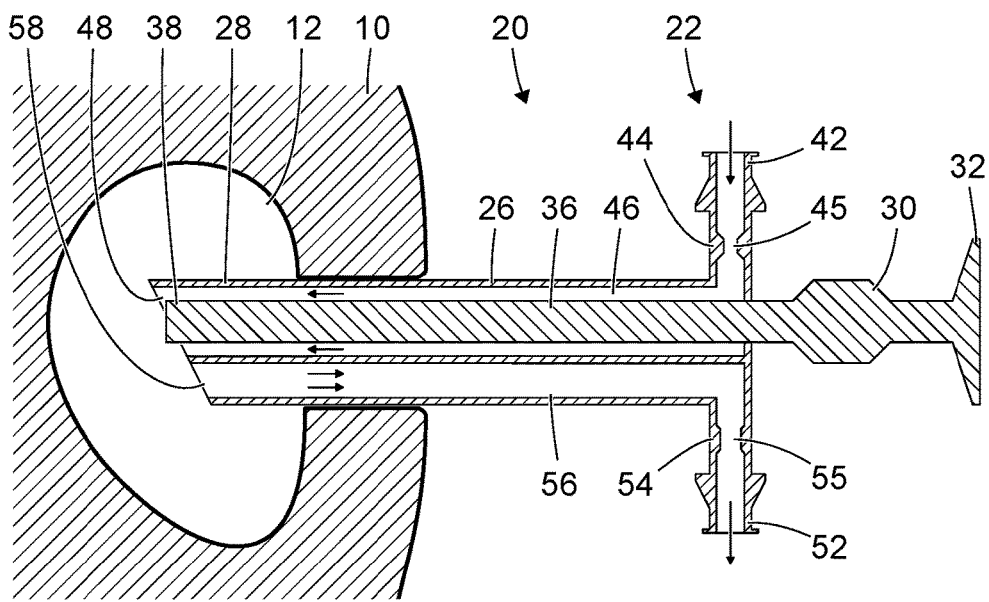
Figure 2:
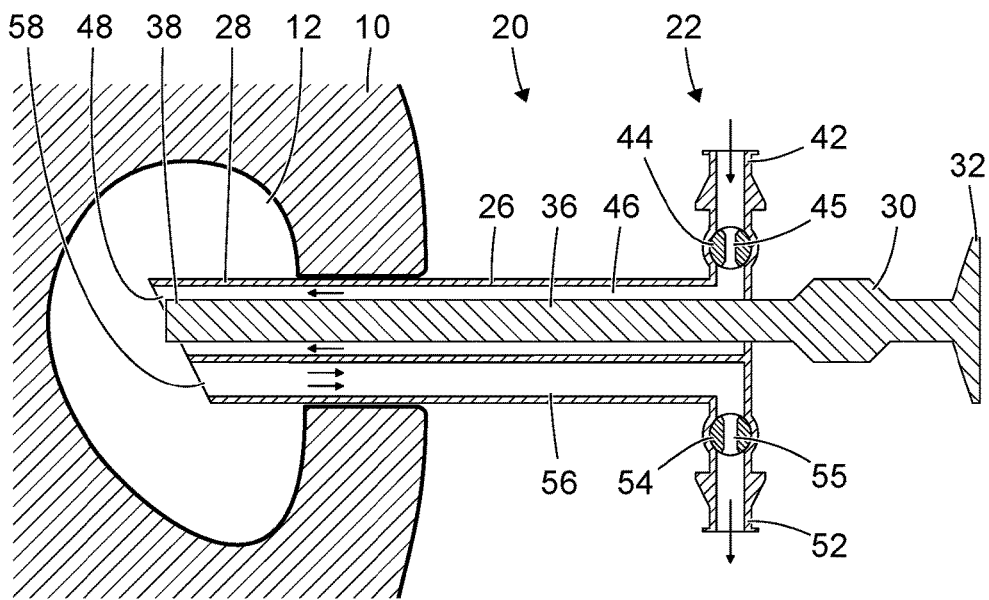
Figure 3:
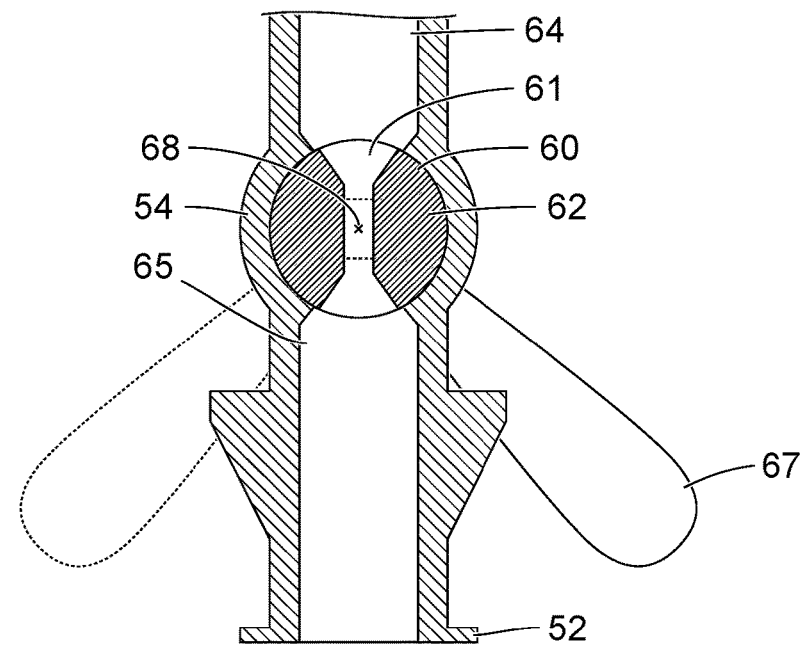
Figure 4:
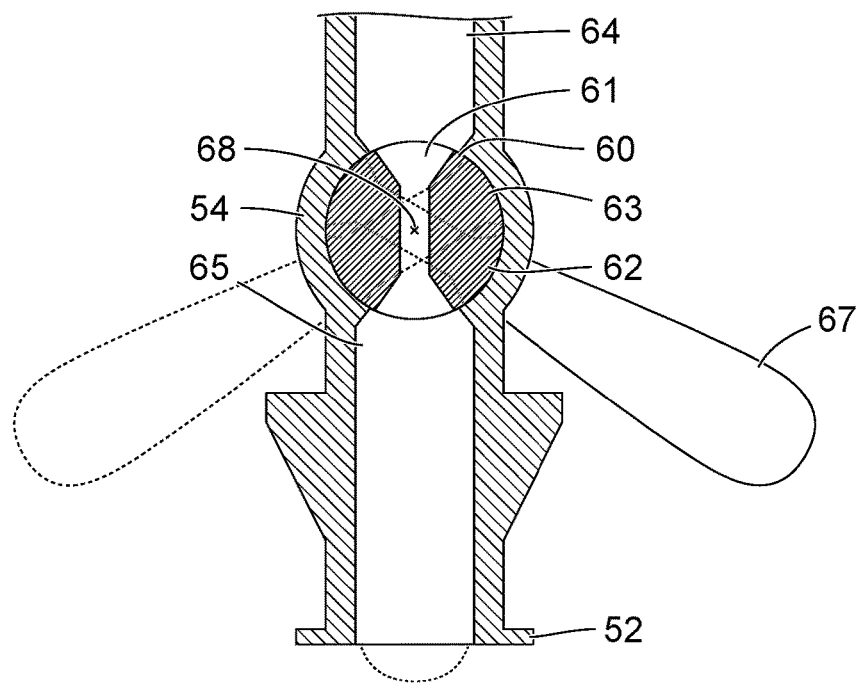
Figure 5:
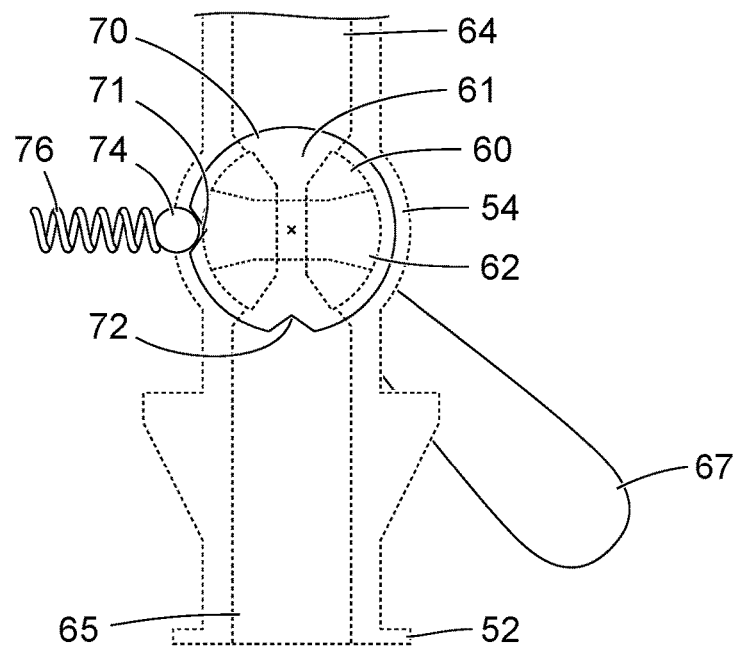
Figure 6:
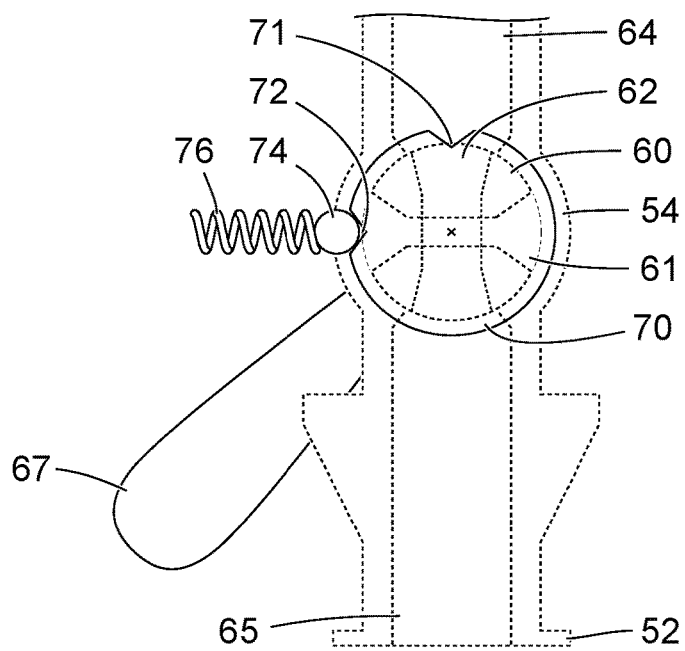
Figure 7:
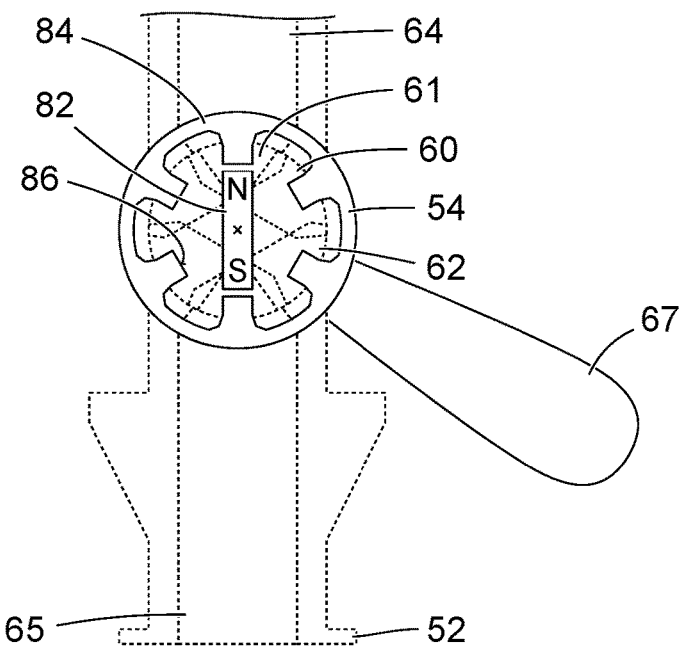
Figure 8:
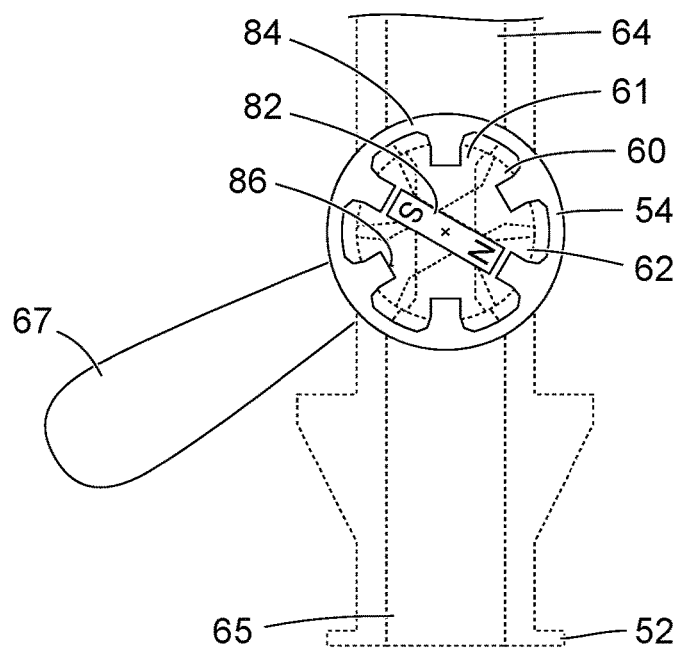
Figure 9:
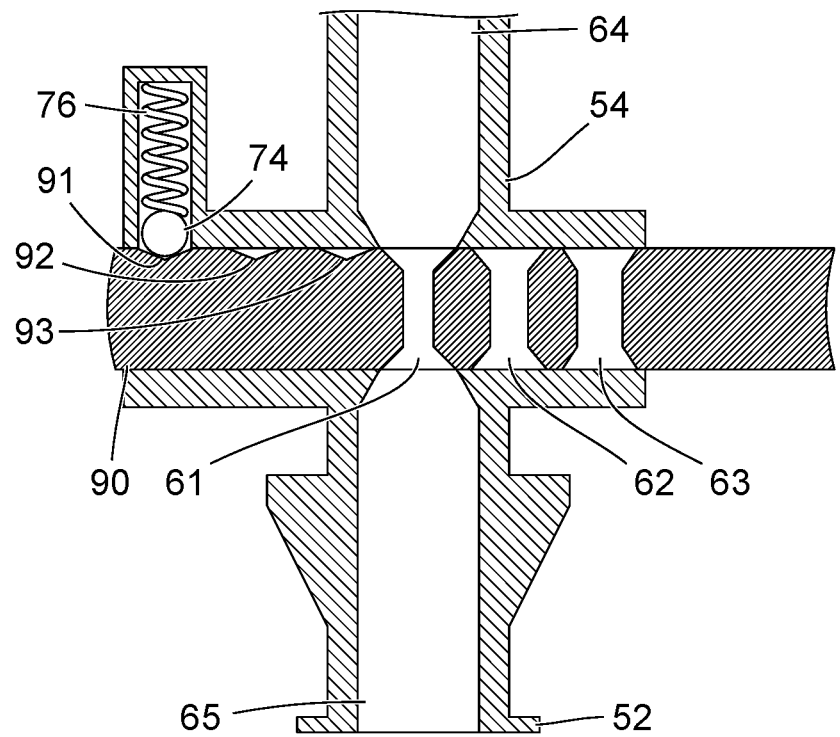
Figure 10:
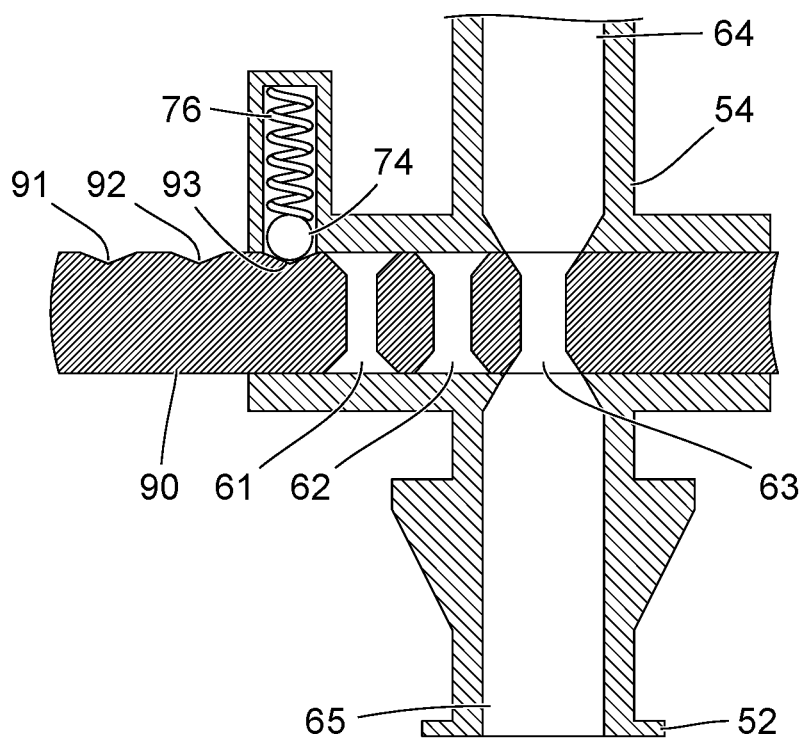

Embodiments are explained below in more detail with reference to the attached figures, in which:

FIG. 1 shows a schematic view of a medical instrument;

FIG. 2 shows a schematic view of a further medical instrument;

FIG. 3 shows a schematic view of a flow resistance means;

FIG. 4 shows a schematic view of a further flow resistance means;

FIG. 5 shows a schematic view of a variant of the flow resistance means from FIG. 3;

FIG. 6 shows a further schematic view of the flow resistance means from FIG. 5;

FIG. 7 shows a schematic view of a variant of the flow resistance means from FIG. 4;

FIG. 8 shows a further schematic view of the flow resistance means from FIG. 7;

FIG. 9 shows a schematic view of a further flow resistance means;

FIG. 10 shows a further schematic view of the flow resistance means from FIG. 9.

DETAILED DESCRIPTION

DESCRIPTION OF THE EMBODIMENTS

FIG. 1 shows a schematic view of a section through a body 10 of a patient and through a medical instrument 20. The section plane of FIG. 1 contains a longitudinal axis of the medical instrument 20.

The body 10 has a cavity 12. The cavity 12 is, for example, the bladder or another hollow organ or another natural cavity in the body 10 of a patient. Alternatively, the cavity 12 is generated artificially for a diagnostic, therapeutic and/or surgical measure.

The medical instrument 20 comprises a proximal region 22, which is provided and designed for arrangement outside the body 10 of a patient. Among other things, structures for handling and controlling the medical instrument 20 are provided in the proximal region 22 of the instrument 20. These structures can include a work element, which is not shown in FIG. 1. A distal region 28 of the medical instrument 20 is provided and designed for arrangement in the body 10 of a patient and in particular in the cavity 12 in the body 10. The medical instrument 20 comprises a shaft 26, which forms the distal region 28 and which reaches as far as the proximal region 22.

The medical instrument 20 can comprise an endoscope 30 with a proximal end 32 which, for example, is formed by an eyepiece and protrudes from the proximal region 22 of the medical instrument 20. A shaft 36 of the endoscope 30 is arranged in the shaft 26 of the medical instrument 20. A distal end 38 of the endoscope 30 is arranged in the distal region 28 of the medical instrument 20, in particular near the outermost distal end thereof.

The endoscope 30 can be part of the medical instrument 20. The endoscope 30 can be connected to the medical instrument rigidly and such that it cannot be released without destruction. Alternatively, the endoscope 30 can be connected to the medical instrument so as to be releasable without destruction. Alternatively, the medical instrument 20 can be designed for an endoscope 30 without the endoscope 30 being a necessary or permanent component part of the medical instrument 20.

The medical instrument 20 has a first coupling structure 42 in the proximal region 22. The first coupling structure 42 comprises, for example, a Luer coupling or a Luer lock coupling and/or a hose nozzle. By means of the coupling structure 42, the medical instrument 20 is connectable via a hose or another fluid line to a fluid reservoir for the provision of a rinsing fluid.

The medical instrument 20 moreover comprises a first fluid channel 46 in the shaft 26 of the medical instrument. In the example shown, the shaft 36 of the endoscope 30 is arranged inside the shaft 26 of the medical instrument 20 such that the first fluid channel 46 surrounds the shaft 36 of the endoscope 30 like a jacket. To put it another way, the cross section of the first fluid channel 46 has an annular topology and encloses the cross section of the shaft 36 of the endoscope 30.

An opening 48 in the distal region 28 of the medical instrument 20 forms the distal end of the first fluid channel 46 and an outlet through which fluid can pass from the first fluid channel 46 into the cavity 12 in the body 10.

A flow resistance means 44 with a reduced cross section 45 is arranged between the first coupling structure 42 and the first fluid channel 46.

The first coupling structure 42, the first flow resistance means 44, the first fluid channel 46 and the first opening 48 form a supply structure for delivering a fluid, in particular a rinsing liquid or another rinsing fluid, to the cavity 12. The smallest cross-sectional area of the supply structure 42, 44, 46, 48 is present at the reduced cross section 45 of the first flow resistance means 44. The flow resistance of the flow resistance means 44 definitively or substantially determines the flow resistance of the entire supply structure. In particular, the flow resistance of the flow resistance means 44 measures at least half or at least two thirds or at least three quarters or at least four fifths or at least nine tenths of the flow resistance of the entire supply structure 42, 44, 46, 48.

The medical instrument 20 moreover comprises a second coupling structure 52 in the proximal region 22. The second coupling structure 52 comprises in particular a Luer coupling or a Luer lock coupling and/or a hose nozzle. By means of the second coupling structure 52, the medical instrument 20 is connectable by a hose or another fluid line to a container for receiving used rinsing fluid.

A second fluid line 56 is moreover provided in the shaft 26 of the medical instrument 20. A second opening 58 in the distal region 28 of the medical instrument 20 forms the distal end of the second fluid channel 56 and therefore an inlet.

A second flow resistance means 54 with a reduced cross section 55 is provided between the proximal end of the second fluid channel 56 and the second coupling structure 52.

The second opening 58 in the distal region 28 of the medical instrument 20, the second fluid channel 56, the second flow resistance means 54 and the second coupling structure 52 form a discharge structure for discharging a fluid from the cavity 12 in the body 10. The smallest cross-sectional area of the discharge structure 52, 54, 56, 58 is present at the reduced cross section 55 of the second flow resistance means 54. The flow resistance of the discharge structure 52, 54, 56, 58 is therefore definitively or substantially determined by the second flow resistance means 54. In particular, the flow resistance of the second flow resistance means 54 measures at least one tenth or at least one fifth or at least one quarter or at least one third or at least half or at least two thirds or at least three quarters or at least four fifths or at least nine tenths of the flow resistance of the entire discharge structure 52, 54, 56, 58.

In the example shown, the cross-sectional area in the region of the reduced cross section 45 of the first flow resistance means 44 is smaller than the cross-sectional area in the region of the reduced cross section 55 of the second flow resistance means 54. In this way, in particular the flow resistance of the supply structure 42, 44, 46, 48 is greater than the flow resistance of the discharge structure 52, 54, 56, 58.

In the medical instrument 20 shown, the discharge structure 52, 54, 56, 58 cannot be closed. To put it another way, there is no intended configuration or no intended operating state of the medical instrument 20 in which the discharge structure 52, 54, 56, 58 would be closed.

In the intended use of the medical instrument 20, the first coupling structure 42 is connected by means of a hose or another fluid line to a bag or another reservoir for a fresh, sterile rinsing fluid, in particular a rinsing liquid. This reservoir is arranged above the cavity 12. The height difference generates a pressure difference. The pressure difference causes a flow of fluid, indicated by arrows in FIG. 1, into the first coupling structure 42, through the first flow resistance means 44, the first fluid channel 46 and the first opening 48 into the cavity 12. The resulting pressure in the cavity 12 (more precisely the pressure difference between the cavity 12 and the environment) causes an outflow of fluid from the cavity 12 through the second opening 58, the second fluid channel 56, the second flow resistance means 54 and the second coupling structure 52. The second coupling structure 52 is in particular connected by a hose, or another fluid line, to a collecting vessel for the fluid.

If, as is indicated in FIG. 1, the flow resistance of the discharge structure 52, 54, 56, 58 is less than the flow resistance of the supply structure 42, 44, 46, 48, a pressure arises in the cavity 12 that is closer to the pressure present at the second coupling structure 52 than the pressure present at the first coupling structure 42. This low pressure, i.e. low by comparison with many possible configurations of conventional medical instruments, protects the patient.

If, as is indicated in FIG. 1, the discharge structure 52, 54, 56, 58 is not closable, the pressure arising in the cavity 12 cannot reach the pressure present at the first coupling structure 42, in contrast to possible configurations of many conventional medical instruments. The patient is thus protected.

FIG. 2 shows a schematic view of a section through a body 10 of a patient and through a further medical instrument 20 which, in terms of certain features, properties and functions, is similar to the medical instrument shown in FIG. 1. The section plane and the nature of the view in FIG. 2 correspond to those of FIG. 1. Features, properties and functions of the medical instrument 20 shown in FIG. 2 that distinguish it from the medical instrument shown in FIG. 1 are described below in particular.

In the medical instrument shown in FIG. 2, the flow resistance means 44, 54 are designed as valves, in particular as plug valves. In the example shown, the flow resistance of the first flow resistance means 44 is greater than the flow resistance of the second flow resistance means 54. The second flow resistance means 54 has in particular several different configurations with different flow resistances. However, the second flow resistance means 54 is in particular designed such that it cannot be completely closed. To put it another way, fluid is able to flow through the second flow resistance means 54 in each configuration of the second flow resistance means 54 provided for the intended use of the medical instrument 20.

FIG. 3 shows an enlarged schematic view of a section through the second flow resistance means 54, designed as a plug valve, of the medical instrument shown in FIG. 2. The coupling structure 52 adjoining the plug valve 54 is also indicated in FIG. 3. The section plane of FIG. 3 corresponds to the section plane of FIG. 2.

The plug valve 54 comprises a conical member designated as plug 60. The plug 60 is rotatable about its axis 68 of symmetry and rotation arranged orthogonally with respect to the section plane of FIG. 3. The plug 60 has two through-bores 61, 62 with different cross sections. The section plane of FIG. 3 lies inside the first through-bore 61 and outside the second through-bore 62. The second through-bore 62 is therefore only indicated by broken-line contours. The through-bores 61, 62 are each arranged orthogonally with respect to the axis 68 of symmetry and rotation of the plug 60. The ends of the through-bores 61, 62 can be conically shaped, as indicated in FIG. 3, in order to reduce or prevent swirling movements of a fluid flowing through the through-bores 61, 62.

The plug 60 is arranged in a conical bore of corresponding shape between a first fluid channel 64 and a second fluid channel 65. In the position of the plug 60 shown in FIG. 3, the first through-bore 61 connects the fluid channels 64, 65 of the plug valve 54. In a position in which the plug 60 has been rotated through 90 degrees relative to the position indicated in FIG. 3, the second through-bore 62 of the plug 60 connects the fluid channels 64, 65 of the plug valve 54.

A manually actuatable lever 67 is arranged behind the section plane of FIG. 3. The lever 67 is connected rigidly to the plug 60 and is rotatable with the latter about the axis 68 of symmetry and rotation.

The lever 67 is shown twice in different positions in FIG. 3, once with a solid line and once with a broken line. For example, the lever 67 adopts the position shown by a solid line when the plug 60 adopts the position shown in FIG. 3, in which the first through-bore 61 connects the fluid channels 64, 65 of the plug valve 54. When the lever 67 adopts the position shown by a broken line as indicated in FIG. 3, the plug 60 is rotated through 90 degrees relative to the position shown in FIG. 3, such that the second through-bore 62 connects the fluid channels 64, 65 of the plug valve 54 to each other. Since the through-bores 61, 62 of the plug have different diameters and cross sections and therefore different flow resistances, the entire plug valve 54 has different flow resistances in both positions.

The openings of the through-bores 61, 62 can be designed and arranged such that the connection between the fluid channels 64, 65 of the plug valve 54 is at no point completely closed even during the rotation of the plug 60 about the rotation axis 68 between the two intended positions.

The first flow resistance means of the medical instrument 20 shown in FIG. 2 can be identical or similar in design to the plug valve 54 shown in FIG. 3.

FIG. 4 shows a schematic view of a further plug valve 54 which, in terms of certain features, properties and functions, is similar to the plug valve shown in FIG. 3. The nature of the view, in particular the section plane in FIG. 4, corresponds to that of FIG. 3. Features, properties and functions of the plug valve 54 that distinguish it from the plug valve shown in FIG. 3 are described below in particular.

The plug valve 54 shown in FIG. 4 can be part of the medical instrument shown in FIG. 2, specifically part of the supply structure and also part of the discharge structure.

The plug valve 54 shown in FIG. 4 differs in particular from the plug valve shown in FIG. 3 in that the plug 60 has three through-bores 61, 62, 63 with different diameters and cross sections. The through-bores 61, 62 of the plug 60 are arranged in different planes orthogonally with respect to the rotation axis 68 of the plug 60. The section plane of FIG. 4 intersects the first through-bore 61 but not the second through-bore 62 and the third through-bore 63. Therefore, the contours of the second through-bore 62 and of the third through-bore 63 are only indicated by broken lines.

The through-bores 61, 62, 63 extend in different directions. In particular, the longitudinal axes of the through-bores 61, 62, 63 are spaced apart from each other by 60 degrees.

FIG. 4 indicates three different positions of the lever 67 connected rigidly to the plug 60. In the position of the lever 67 shown with a solid line, the plug 60 adopts the position shown in FIG. 4. The first through-bore 61 connects the fluid channels 64, 65 of the plug valve 54. In the other two positions of the lever 67 indicated by broken lines (one of which is largely concealed by the coupling structure 42, 52), the plug 60 is rotated through 60 degrees and 120 degrees, respectively, relative to the position shown in FIG. 4. Accordingly, it is not the first through-bore 61 but the second through bore 62 and the third through-bore 63 that connect the fluid channels 64, 65 of the plug valve 54.

Since the through-channels 61, 62, 63 have different diameters and cross sections and therefore different flow resistances, the entire plug valve 54 has different flow resistances in the three configurations.

FIG. 5 shows a schematic view of a variant of the plug valve 54 shown in FIG. 3. The drawing plane of FIG. 5 is parallel to the section plane of FIG. 3. The features already disclosed with reference to FIG. 3 are largely indicated merely by broken contours.

The variant of the plug valve 54 shown in FIG. 5 has a largely circular disk 70 connected rigidly to the plug 60. On its outer circumference, the disk 70 has two grooves 71, 72. Moreover, the plug valve 54 comprises a ball 74 and a spring 76 which are arranged in a blind bore (not shown in FIG. 5) in a housing portion (not shown in FIG. 5) of the plug valve 54. The helical spring 76 presses the ball 74 against the outer circumference of the disk 70.

In the configuration shown in FIG. 5, the ball 74 lies in the first groove 71 on the outer circumference of the disk 70. The engagement of the ball 74 in the first groove 71 holds the disk 70, and with it also the plug 60 and the lever 67, in the position indicated in FIG. 5. A rotation of the lever 67, of the plug 60 and of the disk 70 away from the position indicated in FIG. 5 assumes a deflection of the ball 74 from the position shown in FIG. 5 and a compression of the helical spring 76.

FIG. 6 shows a further schematic view of the plug valve 54 from FIG. 5. In the configuration shown in FIG. 6 and in the positions of the lever 67, of the plug 60 and of the disk 70 shown in FIG. 6, the ball engages in the second groove 72 on the outer circumference of the disk 70. The second through-bore 62 connects the fluid channels 64, 65 of the plug valve 54.

The grooves 71, 72 on the outer circumference of the disk 70, the ball 74 and the helical spring 76 thus act as a latching structure. The latching in the positions indicated in FIGS. 5 and 6 can be felt by the user and simplifies the adjustment of the two alternative predetermined configurations.

In a departure from the view in FIGS. 5 and 6, the grooves 72 on the outer circumference of the disk 70 can be configured (in particular with such a depth) such that their edges adjoin each other, i.e. there is no circular arc-shaped region of the surface of the disk 70. In this case, the force generated by the helical spring 76 and applied to the ball 74 in each position between the positions indicated in FIGS. 5 and 6 can cause a movement of the disk 70 and therefore also of the plug 60 and of the lever 67 toward one of the two predetermined positions shown in FIGS. 5 and 6.

FIG. 7 shows a schematic view of a variant of the plug valve 54 shown in FIG. 4. The nature of the view in FIG. 7 corresponds to that of FIGS. 5 and 6.

In the variant of the plug valve 54 shown in FIG. 7, the plug 60 is rigidly connected mechanically to a magnet 82. A magnetic flux conductor 84 is arranged around the magnet 82. The magnetic flux conductor 84 is formed, for example, from a soft-magnetic iron-containing material. The magnetic flux conductor 84 has a substantially circular or polygonal basic structure. In a departure from an ideal circular shape, the magnetic flux conductor 84 has pole surfaces 86 directed radially inward to the magnet 82 and the rotation axis 68. The pole surfaces 86 are arranged opposite each other in pairs such that, in several predetermined positions of the magnet 82 and therefore also of the plug 60 and of the lever 67 which are rigidly connected to the magnet 82, both poles of the magnet 82 in each case lie opposite a pole surface 86 of the magnetic flux conductor 84. These configurations are preferable in terms of energy. The magnet 82 and the magnetic flux conductor 84 with the pole surfaces 86 thus form a latching structure which defines several predetermined positions of the magnet 82, of the plug 60 and of the lever 67.

FIG. 8 shows a further schematic view of the plug valve 54 from FIG. 7. The nature of the view corresponds to that of FIG. 7. In FIG. 8, the plug valve 54 is shown in a further configuration, which is obtained from the configuration shown in FIG. 7 by rotating the lever 67, the plug 60 and the magnet 82 about the rotation axis 68. The magnet 82, the plug 60 and the lever 67 are held magnetically in both configurations or positions shown in FIGS. 7 and 8. A magnetic latching moment has to be overcome in order to move the lever 67 and with it the plug 60 and the magnet from one of the positions, preferred in terms of energy, to another one.

FIG. 9 shows a schematic view of a section through a further flow resistance means 54, which can be a component part of the medical instrument shown in FIG. 2, in the supply structure or discharge structure thereof. The nature of the view corresponds to that of FIGS. 3 and 4. Features, properties and functions in which the flow resistance means 54 shown in FIG. 9 differs from the flow resistance means shown in FIGS. 3 to 8 are described below in particular.

The flow resistance means 54 shown in FIG. 9 has a slide 90 instead of a plug. The slide 90 is guided in a corresponding channel in the flow resistance means 54 with little play and friction, such that the slide 90 can be moved along a straight path. The slide 90 has several through-bores 61, 62, 63 with different cross sections and accordingly different flow resistances.

Moreover, the slide 90 has several grooves 92. A latching ball 74 and a helical spring 76 are arranged in a blind bore in the housing of the flow resistance means 54, said blind bore being open toward the slide 90. In predetermined positions of the slide 90, the latching ball 74 engages in one of the grooves 92. At the same time, one of the through-bores 61, 62, 63 (the first through-bore 61 in the configuration shown in FIG. 9) connects two fluid channels 64, 65 of the flow resistance means 54. The configuration of the flow resistance means 54, namely the position of the slide 90, can be moved manually between the positions defined by the engagement of the ball 74 in the grooves 91, 92, 93.

FIG. 10 shows a further schematic view of the flow resistance means 54 from FIG. 9. The nature of the view corresponds to that of FIG. 9.

FIG. 10 shows the flow resistance means 54 in another configuration, in which another through-bore 63 in the slide 90 connects the fluid channels 64, 65 of the flow resistance means 54.

It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

REFERENCE SIGNS 10 body of a patient
12 cavity in the body 10
20 medical instrument
22 proximal region of the medical instrument 20
26 shaft of the medical instrument 20
28 distal region of the medical instrument 20
30 endoscope
32 proximal end of the endoscope 30
36 shaft of the endoscope 30
38 distal end of the endoscope 30
42 first coupling structure in the proximal region 22
44 first flow resistance means in the proximal region 22, in particular a valve
45 reduced cross section in the first flow resistance means
46 first fluid channel in the shaft 26
48 first opening as outlet of the first fluid channel 46 in the distal region 28
52 second coupling structure in the proximal region 22
54 second flow resistance means in the proximal region 22, in particular a valve
55 reduced cross section in the second flow resistance means
56 second fluid channel in the shaft 26
58 second opening as inlet of the second fluid channel 56 in the distal region 28
60 plug of the valve 54
61 first through-bore in the plug 62, latching structure
62 second through-bore in the plug 62, latching structure
63 third through-bore in the plug 62, latching structure
64 first fluid channel of the valve 54
65 second fluid channel of the valve 54
67 lever of the valve 54
68 rotation axis of the plug 60 and of the lever 67
70 substantially circular disk connected to the plug 60
71 first latching groove on the circumference of the disk 70
72 second latching groove on the circumference of the disk 70
74 latching ball
76 helical spring
82 magnet
84 magnetic flux conductor
86 pole surface of the magnetic flux conductor 84
90 slide
91 first latching groove on the outer surface of the slide 90
92 second latching groove on the outer surface of the slide 90

93 third latching groove on the outer surface of the slide 90

The invention claimed is:

1. A medical instrument for diagnostic, therapeutic or surgical measures in a cavity in a body of a patient, comprising:
   a proximal region, which is provided and designed for arrangement outside the body;
   a distal end, which is provided and designed for arrangement inside the cavity in the body;
   a supply structure for delivering a fluid to the cavity, wherein the supply structure reaches from a first coupling in the proximal region of the medical instrument to an axial outlet in the distal end;
   a discharge structure for discharging a fluid from the cavity, wherein the discharge structure reaches from an inlet in the distal end of the medical instrument to a second coupling in the proximal region of the medical instrument;
   wherein a flow resistance of the supply structure is greater than a flow resistance of the discharge structure;
   wherein the first coupling of the supply structure has a flow resistance means which substantially determines the flow resistance of the supply structure, or
   the second coupling of the discharge structure has a flow resistance means which substantially determines the flow resistance of the discharge structure;
   wherein the flow resistance means has a finite number of alternative predetermined configurations with different flow resistances, and
   the flow resistance means is provided and designed to be operated exclusively in the predetermined configurations.

2. The medical instrument as claimed in claim 1, in which the discharge structure is not closable or not unconditionally closable.

3. The medical instrument as claimed in claim 1, wherein a smallest cross-sectional area of the supply structure or of the discharge structure is present in the flow resistance means.

4. The medical instrument as claimed in claim 1, in which the flow resistance means has an adjustable flow resistance.

5. The medical instrument as claimed in claim 1, wherein at least one of the flow resistance means of the supply structure and the flow resistance means of the discharge structure comprises a plug valve.

6. The medical instrument as claimed in claim 1, further comprising a shaft extending from the proximal region to the distal end and wherein the supply structure and the discharge structure are positioned within the shaft.

7. The medical instrument as claimed in claim 6, wherein the supply structure comprises a first fluid channel in the shaft and the discharge structure comprises a second fluid channel in the shaft.

8. The medical instrument as claimed in claim 7, wherein the first fluid channel comprises a first diameter, wherein the second fluid channel comprises a second diameter and wherein the first diameter is larger than the second diameter.

9. The medical instrument as claimed in claim 7, further comprising an endoscope and wherein the endoscope is positioned within the first fluid channel.

10. The medical instrument as claimed in claim 7, wherein the flow resistance means of the supply structure is positioned about the first fluid channel.

11. The medical instrument as claimed in claim 7, wherein the flow resistance means of the discharge structure is positioned about the second fluid channel.

12. A medical instrument for diagnostic, therapeutic or surgical measures in a cavity in a body of a patient, comprising:
   a proximal region, which is provided and designed for arrangement outside the body;
   a distal end, which is provided and designed for arrangement inside the cavity in the body;
   a supply structure for delivering a fluid to the cavity, wherein the supply structure reaches from a first coupling in the proximal region of the medical instrument to an axial outlet in the distal end;
   a discharge structure for discharging a fluid from the cavity, wherein the discharge structure reaches from an inlet in the distal end of the medical instrument to a second coupling in the proximal region of the medical instrument;
   a flow resistance means in the supply structure and a flow resistance means in the discharge structure;
   the flow resistance means in the supply structure is in the first coupling or the flow resistance means in the discharge structure is in the second coupling,
   wherein the flow resistance means have a finite number of alternative predetermined configurations with different flow resistances,
   wherein the flow resistance means are provided and designed to be operated exclusively in the predetermined configurations,
   the flow resistance of the flow resistance means of the supply structure is greater than the flow resistance of the flow resistance means of the discharge structure.

13. The medical instrument as claimed in claim 12, in which the flow resistance means have a latching structure which permits only the predetermined configurations of the flow resistance means or which prefers the predetermined configurations over other configurations.

14. The medical instrument as claimed in claim 12, in which
   the flow resistance means have a rotatable member, or a member movable along a straight or curved path, with several through-bores,
   fluid can flow through one or more of the through-bores in each predetermined configuration of the flow resistance means.

15. The medical instrument as claimed in claim 14, in which
   the through-bores have different cross sections,
   fluid can flow through one of the through-bores in each predetermined configuration of the flow resistance means.

16. The medical instrument as claimed in claim 12, in which
   the flow resistance means of the discharge structure does not completely close the discharge structure in any possible configuration or any intended configuration of the medical instrument, or
   the flow resistance means of the discharge structure does not unconditionally completely close the discharge structure in any possible configuration or any intended configuration of the medical instrument.

17. The medical instrument as claimed in claim 12, in which a minimal cross section of the flow resistance means of the supply structure is smaller than a minimal cross section of the flow resistance means of the discharge structure.

* * * * *